United States Patent
Bowen et al.

(10) Patent No.: US 6,638,591 B2
(45) Date of Patent: Oct. 28, 2003

(54) MEMBRANE PERMEABLE TO AROMATIC PRODUCTS

(75) Inventors: William E. Bowen, Neenah, WI (US); Lee J. Murray, Appleton, WI (US); Patricia M. McCarry, Neenah, WI (US)

(73) Assignee: Pechiney Emballage Flexible Europe (FR)

( * ) Notice: Subject to any disclaimer, the term of this patent is extended or adjusted under 35 U.S.C. 154(b) by 0 days.

(21) Appl. No.: 09/730,090

(22) Filed: Dec. 5, 2000

(65) Prior Publication Data
US 2001/0000235 A1 Apr. 12, 2001

Related U.S. Application Data

(63) Continuation of application No. 09/135,196, filed on Aug. 17, 1998, which is a continuation-in-part of application No. 08/475,699, filed on Jun. 7, 1995, now Pat. No. 5,804,264.

(51) Int. Cl.⁷ ............................. B32B 7/06; A61L 9/04
(52) U.S. Cl. .................. 428/41.8; 428/458; 428/475.2; 428/475.8; 239/6; 239/34
(58) Field of Search .............................. 428/520, 516, 428/483, 475.8, 476.1, 476.3, 461, 35.3, 35.4, 35.9, 41.8, 41.7, 42.2, 458, 475.2; 239/6, 43, 57, 34

(56) References Cited

U.S. PATENT DOCUMENTS

| | | | |
|---|---|---|---|
| 4,145,001 A | 3/1979 | Weyenberg et al. ......... 239/56 |
| 4,634,614 A | 1/1987 | Holzner ...................... 428/35 |
| 4,849,606 A | 7/1989 | Martens, III et al. ....... 219/271 |
| 4,886,690 A | * 12/1989 | Davis et al. ............... 428/36.6 |
| 5,491,019 A | 2/1996 | Kuo .......................... 428/213 |
| 5,919,547 A | * 7/1999 | Kocher et al. ............. 428/138 |

* cited by examiner

*Primary Examiner*—D. Lawrence Tarazano
(74) *Attorney, Agent, or Firm*—McDermott, Will & Emery

(57) ABSTRACT

A multilayer structure with improved permeation for atmospheric diffusion of aromatic products wherein the structure comprises, a permeable membrane wherein said permeable membrane comprises at least two polymeric layers wherein the polymer of each layer is independently selected from the group consisting of polyethylene, very low density polyethylene, low density polyethylene, ethylene methylacrylate copolymer; a release layer wherein said release layer comprises a nylon polymer or a ethylene vinyl alcohol copolymer wherein the release layer is adhered to most inner polymeric layer of the permeable-member which comprises the permeable membrane and wherein the adhesion between release layer and the adjacent layer of the polymeric permeable membrane is a relatively weak bond compared to the bond between the layers of the polymeric permeable membrane; and an impermeable membrane wherein said impermeable membrane comprises one or more layers wherein the materials which comprise the individual layers of the impermeable membrane are independently selected from metal or foil and wherein said impermeable portion is laminated to said release layer.

1 Claim, 3 Drawing Sheets

MEMBRANE PERMEABLE TO AROMATIC PRODUCTS

This application is a continuation U.S. application Ser. No. 09/135,196, filed Aug. 17, 1998, now pending which is a continuation-in-part of application Ser. No. 08/475,699, filed Jun. 7, 1995, now U.S. Pat. No. 5,804,264.

BACKGROUND OF THE INVENTION

1. Field of the Invention

The present invention pertains, generally to the field of permeable membranes and packaging for volatile materials, such as fragrances and other aromatic products, and more particularly, to permeable multilayer membranes and packages, which allow the controlled release of aromatic products over a period of time. The package prevents the escape of the aromatic fragrance until the consumer desires to start the release of the fragrance by peeling back the package to expose the permeable membrane.

2. Description of the Art

The controlled time release of very volatile substances, such as fragrances and other aromatic products, presents a number of packaging problems. Room "air fresheners" or fragrances have usually been packaged in glass bottles or vials. The fragrance is released into the atmosphere by transmission through an absorbent wick, which is capped until the time of use. However, glass bottles are bulky and breakable. It is generally not economical to package fragrances in small quantities inside glass containers, because the cost of the glass container is high.

One proposed alternative method of packaging room fragrances is to place a breakable glass vial within a plastic container formed of a material that is permeable to the vapors of the volatile fragrance. The user deliberately breaks the glass vial to allow the fragrance liquid to seep into the absorbent pad and the vapors from the liquid slowly diffuse into the atmosphere through the permeable outer container. These containers may be subject to accidental breakage of the glass vial during shipping and handling, as well as to a possible puncture of the container by broken glass. The manufacturing costs are increased by the use of the glass vial within the container.

Other fragrance dispensers utilize sealed packages, which are opened by peeling back a covering foil to expose a perforated panel covering an absorbent pad filled with the fragrance liquid. The costs of such containers make them generally inappropriate for dispensing small amounts of the fragrance. It is also somewhat difficult to obtain controlled release of the fragrance at a fairly constant rate over the life of the product, because the liquid is directly exposed to the atmosphere. In addition, the consumer may come into contact with the fragrance liquid, because the fragrance liquid may seep through the holes in the perforated panel.

Many other common packaging materials, including some plastic films, are permeated by the fragrance before the desired release or are subject to attack by the fragrance itself or by its liquid carrier.

U.S. Pat. No. 4,634,614 issued to Holzner, relates to a peel system for a device for perfuming ambient air. The peel system comprises a delamination of a paper layer to separate a non-permeable lidding from a permeable membrane. In this invention, the paper layer does not provide a barrier to the aromatic product and some of the aromatic product is allowed to escape with time. In addition, the exposed membrane often has a poor appearance, as paper fibers may be left on the membrane when the package is peeled to activate the fragrance.

U.S. Pat. No. 4,145,001 issued to Weyenberg et al., and incorporated herein by reference, discloses a dispenser having a permeable membrane. The fragrance is sandwiched between the inner layers of two heat sealable panels. One of the inner layers is permeable to the fragrance vapors. The outer layers of the panels are impermeable to the fragrance and its vapors. The dispenser is opened by peeling back a panel along a release layer to expose the inner permeable layer. However, the permeable membrane layer disclosed in U.S. Pat. No. 4,145,001 has limited permeation for certain fragrances.

Other problems associated with permeable membranes are problems with machine operations. The most effective resins for permeation are often tacky in nature. The tacky nature of these resins often cause problems with the operation of the package machinery and processing steps, such as laminating, slitting and converting.

One objective of the present invention is an improved permeable multilayer membrane that provides greater controlled release over an extended period of time and increased permeation for a broader range of fragrances. Another objective is a multilayer membrane, which allows for the special selection of resins in the machine and tie layers to prevent problems associated with the operation of the package machinery and processing steps. Another objective of the present invention is to provide packaging for the fragrances and a means for exposing the membrane to the atmosphere at a desired time by consumer manipulation. A still further objective is to provide a release layer that has improved barrier to fragrances.

SUMMARY

This invention relates to an improved permeable membrane for volatile substances, such as a room air fresheners, fragrances and other aromatic products, that satisfies the need for a permeable membrane which provides greater controlled release and increased permeation for a broad range of fragrances. This invention also relates to the packaging of the improved permeable membrane and to provide a means for exposing the membrane to the atmosphere at a desired time by consumer manipulation. This invention also relates to an improved release layer that aids in containing the fragrance until the packaging is opened.

In one embodiment of the present invention, the invention is a coextruded multilayer structure comprising a permeable membrane and a release layer. The membrane comprises a first permeable sealable layer, a second permeable layer. The release layer is adhered to the second layer. The adhesion between the release layer and the second layer is a relatively weak bond compared to the bond between the first and second layers. The bond strength is controlled by the selection of the resins in the second layer and the release layer.

The first layer includes polymers, such as polyethylene, poly(ethylene vinyl acetate) (EVA) and other heat sealable permeable resins. The second layer includes polymers such as polyethylene, poly(ethylene vinyl acetate) and others that can be blended or modified to produce a strong bond to the first layer and a relatively weak bond to the release layer. The release layer includes a polymer or copolymer such as nylon or ethylene vinyl alcohol copolymer (EVOH).

The ethylene vinyl alcohol of the present invention has a ethylene content of less than forty percent. The nylons of the present invention include poly($\epsilon$-caprolactam)/nylon-6; and poly(hexamethylene)/nylon-6,6.

In another embodiment of the present invention, the invention is a coextruded multilayer structure comprising a permeable membrane and a release layer. The membrane comprises a first permeable sealable layer, a second permeable layer adhered to the first layer and a third permeable layer adhered to the second layer. The release layer is adhered to the third layer. The adhesion between the release layer and the third layer forms a relatively weak bond as compared to the adhesion between the first and second layers and the adhesion between the second and third layers.

The first layer includes a polymer, such as polyethylene, (poly(ethylene vinyl acetate) (EVA) and other heat sealable permeable resins. The second layer comprises semi crystaline polymers. The third layer is selected from resins that provide a high (strong) degree of bond to the second layer and controllable relatively weak bond to the release layer. The release layer includes a polymer, or copolymer such as nylon or EVOH resins.

In another embodiment of the present invention, the invention is a coextruded multilayer structure comprising a permeable membrane and a release layer. The membrane comprises a first permeable sealable layer, a second permeable layer adhered to the first layer, a third permeable layer adhered to the second layer and a fourth permeable layer adhered to the third layer. The release layer is adhered to the fourth layer. The adhesion between the release layer and the fourth layer forms a relatively weak bond as compared to the adhesion between the first and second layers, the adhesion between the second and third layers and the adhesion between the third and fourth layers. The release layer also cooperates with the impermeable layers to contain the product.

The first layer includes a polymer, such as polyethylene, EVA blends including very low density polyethylene (VLDPE) and other heat sealable resins. The second and fourth layers are selected from resins that provide a high degree of bond to the first and third layers and a controllable relatively weak bond to the release layer. The third layer comprises resins with high permeability to gases and aromatic compounds. The release layer includes a polymer, such as a homopolymer or copolymer of nylon or EVOH.

In another preferred embodiment of the invention, the coextruded multilayer structure is incorporated into a package. The package holds an aromatic product between two heat sealable panels. One of the panels can be manipulated to remove certain impermeable layers to expose a permeable membrane to the atmosphere, which allows for the escape of the vapors from the aromatic product.

The first heat sealable panel is a laminated structure. It comprises a permeable membrane, a release layer and an impermeable portion. The permeable membrane comprises a first permeable sealable layer, a second permeable layer adhered to the first layer and a third permeable layer adhered to the second layer. The release layer is adhered to the third layer of the permeable membrane. The release layer is relatively impermeable to most products and cooperates with the impermeable layers to contain the product.

The impermeable portion comprises one or more impermeable layers and is selected to be impermeable to the aromatic product and its vapors, so that no significant amount of vapors will escape while the package is sealed. The impermeable portion is laminated to the release layer opposite the permeable membrane.

The second heat sealable panel is a laminated structure comprising one or more impermeable layers, which are selected to be impermeable to the aromatic product and its vapors, so that the vapors will not escape while the package is sealed.

The aromatic product is disposed between the first sealable layer of the membrane in the first heat sealable panel and an outer layer of the second heat sealable panel. The first sealable layer of the membrane and the outer layer of the second panel are heat sealed together in a bond formed around the aromatic product.

The heat bonding around the aromatic product is preferably accomplished by pressing all of the layers of the package between a hot die and a resilient backing. In such a case, the release layer of the first heat sealable panel is selected of a material which will form only a weak heat bond with the third permeable layer of the membrane. The adhesion of the weak heat bond is substantially less than the adhesion of the bond between the second and third layers of the membrane and the first and second layers of the membrane. The adhesion of the bond is also less than the adhesion of the bond between the first sealable layer of the membrane and the outer layer of the second panel.

Preferably, the first sealable layer of the membrane and the outer layer of the second panel are not adhered together, except at the heat bond area. This allows the layers of the package to be easily pulled away from each other by the user between the two heat sealable panels up to the area of the bond. As the package is pulled by the user to the area of the heat bond, the first sealable layer of the membrane will split at the heat bond and remain bonded to the outer layer of the second panel. The release layer will part from the third layer of the membrane to allow the release layer and the impermeable layers of the first heat sealable panel to be removed. This leaves the aromatic product covered on one side by only the permeable membrane and allows the vapors from the aromatic product to diffuse through the permeable membrane into the atmosphere at a fairly constant rate over a period of time.

The process of heat bonding the layers of the package together is preferably accomplished by using a die having a lip or protrusion extending slightly beyond the face of the remainder of the die. When such a die is pressed onto the package layers and against a resilient backing, the first sealable permeable layer of the membrane and the outer layer of the second panel will soften and spread apart from the line of the protrusion on the die to form a line of weakness. This line of weakness is advantageous in allowing the membrane to split easily as the package is peeled open by a user. To ensure the structural integrity of the package, it is preferable that the impermeable layers are formed of a material which will not melt at the temperature of the bonding die.

For optimum performance of the package, it is also preferred that the line of weakness, and the wider heat bond adjacent to it, be formed in a V or a chevron shape at a position spaced away from one end of the package. The user easily peels open the package up to the point of the chevron, with the weakened permeable layers splitting at the chevron to allow the remainder of the package to be peeled apart. The remainder of the heat seal surrounding the aromatic product is sealed over a broad area without forming a line of weakness.

The package of this invention has the desirable feature of being relatively light and has no breakable parts, which could be dangerous. The package is very inexpensive to manufacture and is suitable for dispensing small quantities of fragrances. As long as the package remains sealed, the volatile fragrance cannot escape; thus, allowing a very long shelf life for the product. Special precautions during the handling of the product are unnecessary, since there are no parts that can be broken or easily damaged. Once the package has been opened by the consumer, the volatile vapors diffuse through the permeable membrane at a controlled and selected rate. Because the process of transfer through the permeable layer is a diffusion process, rather than direct evaporation, the rate of release of the vapor is relatively uniform over the expected life of the package.

In a preferred process for producing the package, the layers of the permeable membrane and the release layer are cast coextruded to form a very uniform but weak bond between the membrane and the release layer. The impermeable portion of the first panel is then adhered to the release layer using an adhesive, which provides a long lasting and uniform bond between the two materials. The two heat sealable panels may then be brought together over the aromatic product with a heated die being impressed over the two panels of the package to form a heat bond between them that surrounds and seals the aromatic product. Various materials, such as metal foil, may be used for the impermeable portion, and in such case it is desirable to protect the outer surface of the foil layer(s) by adhering a tough protective layer thereto.

In the case of some aromatic products the release layer can be selected to have sufficient barrier to the product to eliminate the need for foil or other high barrier layers in the non-permeable portion of the top panel. The panel is typically constructed with reverse printed polyethylene tertphthalate (PET) film as the outer most layer. A barrier layer located between the permeable membrane layers and the printed surface is required not only to contain the produce prior to use but dually protects the printing from product attack. The barrier requirement is a function of the chemical formulation of the product and the required shelf life prior to use. Certain products contain fragrance oils or carriers such as iso-par that permeate more readily than other formulations and thus require greater barrier. This is particularly true if the product must be contained for 1–2 years before use.

In another preferred embodiment of the present invention, the coextruded multilayer structure is incorporated into a package. The package holds an aromatic product between two heat sealable panels. A first heat sealable panel can be manipulated to remove certain impermeable layers to expose a permeable membrane to the atmosphere, which allows for the escape of the vapors from the aromatic product. The first heat sealable panel comprises a four layer permeable membrane, a release layer-which is somewhat impermeable and an most impermeable portion. The impermeable portion comprises one or more impermeable layers. The permeable membrane comprises a first permeable sealable layer, a second permeable layer adhered to the first layer, a third permeable layer adhered to the second layer and a fourth permeable layer adhered to the third layer. The release layer is adhered to the fourth layer of the permeable membrane and the, impermeable portion is laminated to the release layer opposite the permeable membrane.

A second heat sealable panel is a laminated structure comprising one or more impermeable layers, which are selected to be impermeable to the aromatic product and its vapors, so that the vapors will not escape while the package is sealed.

The aromatic product is disposed between the first sealable layer of the membrane in the first heat sealable panel and an outer sealable layer of the second heat sealable panel. The first sealable layer of the membrane and the outer layer of the second panel are heat sealed together in a bond formed around the aromatic product.

In another preferred embodiment of the invention, the second heat sealable panel comprises a thermoform tray. The first sealable layer of the membrane is heat sealed to the thermoform tray to cover the tray.

These and other features, aspects and advantages of the present invention will be apparent from the following detailed description, appended claims and accompanying drawings showing preferred embodiments of the present invention.

BRIEF DESCRIPTION OF THE DRAWINGS

The invention will be further described in connection with the accompanying drawings, in which.

DESCRIPTION

Figure 1A:
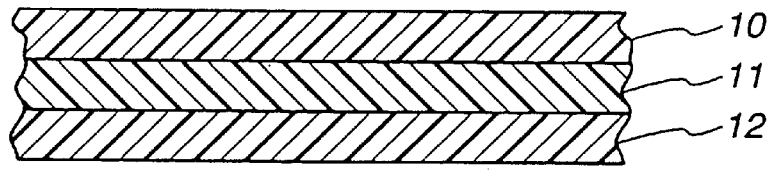
FIG. 1a & FIG. 1b are cross-sections of embodiments of a multilayer structure of this invention.

Referring to the drawings, an embodiment of the invention is shown generally in FIG. 1a. The multilayer structures comprises a first sealable permeable layer 10, a second permeable layer 11 adhered to the first layer 10 and a release layer 12 adhered to the second layer 11. Layers 10 and 11 form the permeable membrane. Layer 12 is coextruded with the membrane layers and has two functions. First as the release layer it cooperates with the permeable layers to provide a designed peel or delamination. Second, the release layer offers a barrier to the aromatic product.

Layer 10 is permeable and cooperates with layer 11 to provide the desired permeability of the membrane. Layer 10 comprises polymers and other components that provide permeability properties, good heat seal properties and machinability. Examples of materials that are suitable for layer 10, include polyethylene, EVA, poly(ethylene vinylacetate) or other sealable resins. Machine aids, such as slip and antiblock may also be added to this layer.

Layer 11 is a permeable layer that forms a tie between layers 10 and 12. Layer 11 is formed of resins that form a strong bond to layer 10 and the desired relatively weak bond to layer 12. Examples of materials that are suitable for layer 11, include: polyethylene, EVA, or other modified resins such as those modified with maleic anhydride. In a preferred embodiment, layer 12 is nylon or EVOH and layer 11 is a blend of LDPE and a modified polyolefin such as those sold by Equistar under the trade name "Plexar" or those sold by Mitsui under the trade name, "ADMER".

Layer 12 is the release layer and cooperates with layer 11 to form the peel function. Layer 12 provides barrier to the aromatic product. The release layer 12 may be homopolymer or copolymers of nylon or EVOH. Layers 10 and 11 form the membrane and in one example can have a thickness of 4.0 mils and the release layer a thickness of 1.0 mil.

Figure 1B:
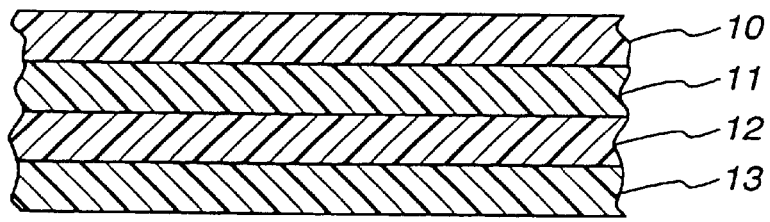

FIG. 1b shows and alternate embodiment that provides an additional membrane layer that allows greater flexibility in choosing resins for particular functions. The multilayer structure comprises a first sealable permeable layer 10, a second permeable layer 11 adhered to the first layer 10, a third permeable layer 12 adhered to the second layer 11 and a release layer 13 adhered to the third layer 12. Layers 10, 11 and 12 form the permeable membrane. Layer 13 is coextruded with the permeable membrane layers and has two functions. First as the release layer it cooperates with the permeable layers to provide a designed peel or delamination. Second, the release layer offers a barrier to the fragrance.

Layer 10 is permeable and cooperates with layers 11 and 12 to provide the desired permeability of the membrane. Layer 10 comprises polymers and other components that provide permeability properties, good heat seal properties and good machinability to the outside layer of the membrane. Examples of materials that are suitable for layer 10, include: polyethylene, EVA or other heat sealable resins. Machine aids, such as antiblock and slip, may also be added to this layer.

Layer 11 forms the bulk of the membrane and has the greatest impact on the permeability of the membrane. Layer 11 is formed of resins having a high permeation rate for the aromatic product. Examples of materials which are suitable for layer 11, include: low density polyethylene (LDPE), very low density polyethylene (VLDPE), EVA, ethylene-methyl acrylate copolymer and other available polymers, particularly semi crystaline polymers. Polymers of VLDPE having a density range between 0.870 g/cc and 0.900 g/cc are especially preferred. Layer 11 may also include blends of these polymers designed for specific diffusion.

Heat of fusion measurements aid in identifying candidate polymers for layer 11, because the heat of fusion data correlates with the gas transmission rates of the polymers. The heat of fusion measurements are obtained from pressed films using a Differential Scanning Calorimeter. Polymers with lower heats of fusion are less crystaline and have higher permeation rates. See Table 1.

TABLE I

| Samp. | Supplier | Type | Grade | Heat of Fusion (1$^{st}$ Heat), J/g |
|---|---|---|---|---|
| F | Dow-DuPont | Engage Octene Plastomer | 8200 | 22.2 |
| I | Exxon | Exact | 4011 | 38.6 |
| G | Chevron | Plastomer | 2205 | 40.9 |
| H | Chevron | Plastomer | 2255 | 43.1 |
| G | Union Carb. | VLDPE | 9042 | 57.5 |
| A | Exxon | Exact | 3027 | 68.2 |
| D | Dow | Affinity SSC LLDPE | 58000.01 | 68.5 |
| B | Exxon | Exact | 3028 | 73.5 |
| E | Dow | Attain ULDPE | 61512.13 | 78.2 |
| C | Exxon | Exact | 3006 | 84.9 |

The degree of permeability of a particular polymer material can be increased by adding impurities, such as calcium carbonate to open up additional spaces between the polymer and the filler. The impurities are added to the polymer material before the membrane is formed. Additional permeability may also be a by-product of coloring the layer by introducing solid micro particles of pigment, which also tends to open up spaces between the polymer and the filler.

Layer 12 is a permeable tie layer. Layer 12 cooperates with layer 11 to provide the desired permeation. Layer 12 is formed from resins that provide a strong bond with layer 11 and a relatively weak bond with the release layer 13 to produce a peel laminate. Selection of the polymer for layer 12 depends upon the polymer selection for layer 13.

In preferred embodiment, layer 13 is nylon or EVOH and layer 12 is a blend of LDPE and a modified polyolefin sold by Equistar under the trade name "PLEXAR" or "ADMER" sold by Mitsui.

Layer 13 is the release layer. Layer 13 cooperates with layer 12 to form the peel function. Layer 13 also provides good barrier properties from the product. The release layer 13 is EVOH or nylon resins.

Layers 10 and 12 are relatively thin as compared to layer 11. In a preferred example, layer 10 is 0.5 mils to 1.0 mils, layer 12 is 0.5 mils to 1.0 mils and layer II is 2.0 mils to 4.0 mils.

The third permeable layer 12 is initially uniformly bonded to a release layer 13 which is composed of a material that does not form strong heat bonds with the third permeable layer 12 at the same temperature at which bonds are formed between permeable layers 10 and 11 and permeable layers 11 and 12. For example, Nylon or EVOH can be utilized as the release layer in conjunction with modified polyethylene or EVA in the third permeable layer. It is further desired to coextrude the permeable membrane layers and the release layer together at a temperature that produces a very uniform but weak bond between the release layer and the permeable membrane.

Figure 2:
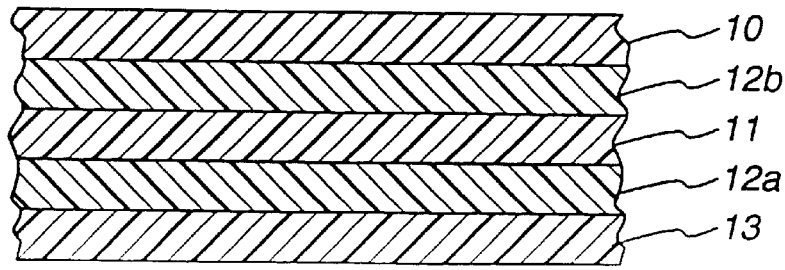
FIG. 2 is a cross-section of another embodiment of a multilayer structure of this invention.

Referring to the drawings, an alternative embodiment of the invention is shown generally in FIG. 2. The multilayer structure comprises a first sealable permeable layer 10, a second permeable layer 12b adhered to the first layer 10, a third permeable layer 11 adhered to the second layer 12b, a fourth permeable layer 12a adhered to the third permeable layer 11 and a release layer 13 adhered to the fourth layer 12a. Layers 10, 11, 12a and 12b form the permeable membrane. Layer 13 is coextruded with the permeable membrane layers and forms the release layer.

Layer 10 is permeable and cooperates with layers 12b, 11 and 12a to provide the desired permeability for the membrane. Layer 10 comprises polymers and other components that provide permeability properties, good heat seal properties and good machinability to the outside layer of the membrane. Examples of materials that are suitable for layer 10, include: polyethylene, poly(ethylene vinyl acetate), very low density polyethylene, or other heat sealable resins or blends of same. Machine aids, such as processing aid, stabilizers, antiblock and slip, may also be added to this layer.

Layer 11 forms the bulk of the membrane and has the greatest impact on the permeability of the membrane. Layer 11 is formed of resins having a high permeation rate for the aromatic product. Examples of materials which are suitable for layer 11, include: LDPE, VLDPE, EVA, ethylene-methyl acrylate copolymer and other available polymers, particularly semi crystaline polymers. Polymers of VLDPE having a density range between 0.870 g/cc and 0.900 g/cc are especially preferred. Layer 11 may also include blends of these polymers.

Layers 12a and 12b cooperate with layer 11 to provide the desired permeability. Layers 12a and 12b are connected internally in the extrusion equipment and are comprised of the same material. Layers 12a and 12b are formed from resins that provide a strong bond to layer 11 and a relatively weak bond to the release layer 13 to produce a peel laminate. Selection of the polymer for layers 12a and 12b depend upon the polymer selection for layer 13. In a preferred embodiment of the invention, layer 13 is nylon or EVOH and layers 12a and 12b are comprised of a modified polyolefin. In another preferred embodiment, layer 13 is nylon or EVOH and layers 12a and 12b are a blend of LDPE and a tie resin e.g. that sold under the trade name "PLEXAW" or a Mitsui resin sold under trade name "ADMER."

Layer 13 is the release layer. Layer 13 cooperates with layer 12a to form the peel function. Layer 13 also provides good barrier properties from the product. The release layer 13 may be EVOH or nylon or copolymers of these resins.

The fourth permeable layer 12a is initially uniformly bonded to a release layer 13. The release layer 13 is comprised of a material that does not form strong heat bonds with the fourth permeable layer 12a at the same temperature at which bonds are formed between permeable layers 10 and 12b, permeable layers 12b and 11 and permeable layers 11 and 12a. For example, nylon or EVOH can be utilized as the release layer in conjunction with a modified polyethylene or EVA fourth permeable layer. It is further desired to coextrude the permeable membrane layers and the release layer material together at a fairly low temperature that produces a very uniform but weak bond between the release layer and the permeable membrane.

Figure 3:
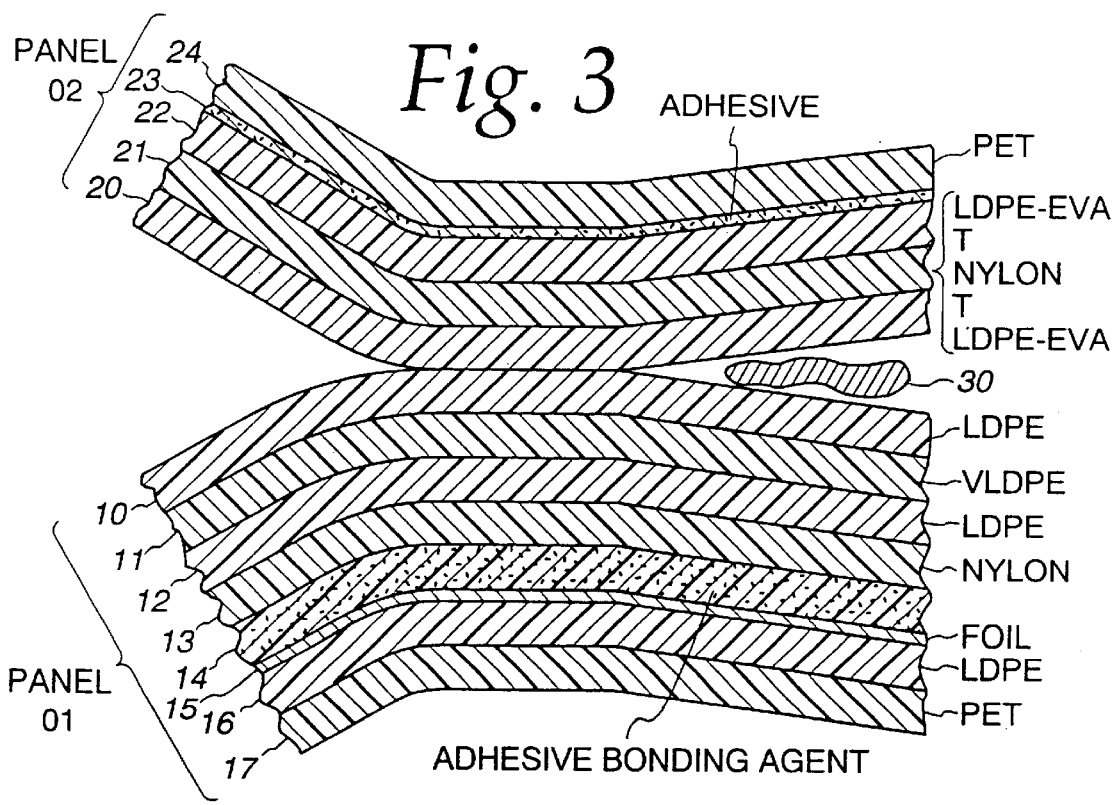
FIG. 3 is a cross-section of a package, in accordance with this invention.

Another preferred embodiment of the invention is shown in FIG. 3. FIG. 3 shows the incorporation of a multilayer permeable membrane into a scent release package. The package comprises two heat sealable panels 01 and 02. Panel 01 comprises a permeable membrane, a release layer and impermeable portion. The permeable membrane is formed by layers 10, 11 and 12. Layer 13 is the release layer. The impermeable portion is comprised of Layers 14, 15, 16 and 17.

The membrane comprises a first sealable permeable layer 10, a second permeable layer 11 adhered to the first layer 10 and a third permeable layer 12 adhered to the second layer 11. The release layer 13 is adhered to the third layer 12. Layer 13 is coextruded with the permeable membrane layers.

Layer 10 is permeable and cooperates with layer 11 to provide the desired permeability. Layer 10 comprises polymers and other components that provide permeability properties, good heat seal properties and good machinability to the outside layer of the membrane. Layer 10 is in contact with the aromatic product 30 and the material selected for layer 10 should have minimum interaction with the product 30. Examples of materials that are suitable for layer 10, include: polyethylene blends with VLDPE EVA other heat sealable resins. Machine aids, such as antiblock, slip, and stabilizers may also be added to this layer.

Layer 11 forms the bulk of the membrane and has the greatest impact on the permeability of the membrane. Layer 11 is formed of resins having a high permeation rate for the aromatic product. Examples of materials which are suitable for layer 11, include: LDPE, VLDPE, EVA, ethylene-methyl acrylate copolymer and other available polymers, particularly semi crystaline polymers. Polymers of VLDPE having a density range between 0.870 and 0.900 g/cc are especially preferred. Layer 11 may also include blends of these polymers.

Layer 12 is a permeable. tie layer. Layer 12 cooperates with layer 11 to provide the desired permeation. Layer 12 is formed from resins that provide a strong bond to layer 11 and a relatively weak bond to the release layer 13 to produce a peel laminate. Selection of the polymer for layer 12 depends upon the polymer selection for layer 13. In a preferred embodiment of the invention, layer 13 is a nylon or EVOH and layer 12 is a modified polyolefin. In another preferred embodiment, layer 13 is a nylon or EVOH and layer 12 is a blend of LDPE and a tie resin, e.g., those sold under the trade names "PLEXAR" or "AMER".

Layer 13 is the release layer. Layer 13 cooperates with layer 12 to form the peel function. Layer 13 also provides barrier properties to the product. The release layer 13 may be copolymer or homopolymer of nylon or EVOH Layers 10 and 12 are relatively thin as compared to layer 11. In a preferred example, layer 10 is 0.5 to 1.0 mils, layer 12 is 0.5 to 1.0 mils and layer 11 is 2.0 to 4.0 mils.

The third permeable layer 12 is initially uniformly bonded to a release layer 13. Release layer 13 comprises a material that does not form strong heat bonds with the third permeable layer 12 at the same temperature at which bonds are formed between permeable layers 10 and 11 and permeable layers 11 and 12. For example, nylon or EVOH can be utilized a the release layer in conjunction with a modified polyethylene or EVA in the third permeable layer. It is further desired to coextrude the permeable membrane layers and the release layer together at a temperature that will produce a very uniform but weak bond between the release layer and the permeable membrane.

Layers 10, 11, 12 and 13 are cast coextruded and comprise a multilayer structure. The structure is laminated to the impermeable portion of panel 01 at layer 13. The impermeable portion of panel 01 comprises layers 14, 15, 16 and 17. These layers are laminated together such that layer 14 is adhered to layer 15, layer 15 is adhered to layer 16 opposite layer 14 and layer 16 is adhered to layer 17 opposite layer 15. Layer 13 is laminated to layer 14 opposite layer 15.

In a preferred embodiment of the invention, the release layer 13 is nylon or EVOH and layer 14 is a laminating adhesive. Layer 15 is foil, layer 16 is a polyethylene laminating resin and layer 17 is a polyester.

Panel 02 is comprised of layers 20, 21, 22, 23 and 24. Layers 20, 21, and 22 form a multilayer nylon coextruded film. In a preferred embodiment, the nylon coextruded film has adhesive or tie layers on either side (adjacent) of the nylon layer. Layer 23 is an adhesive and layer 24 is a polyester, acrylonitrile polymer (BAREX) or a recycled polyester sheet. The nylon coextruded film is laminated to layer 24 by the adhesive layer 23.

The aromatic product 30 is held between layer 10 of panel 01 and layer 20 of panel 02. Layer 10 is heat sealed to layer 20. The bond formed between layer 10 and layer 20 is stronger than the bond formed between layer 12 and release layer 13.

Figure 4:
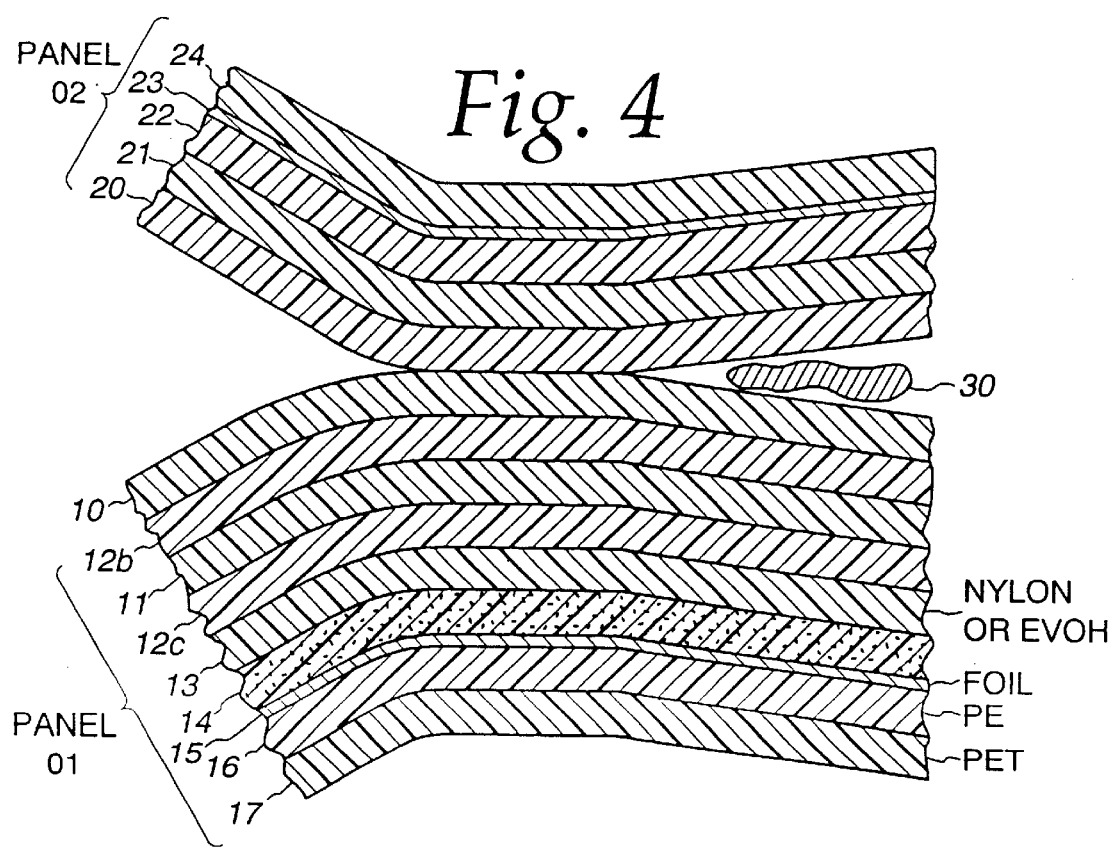
FIG. 4 is a cross-section of another package, in accordance with this invention.

Another preferred embodiment of the invention is shown in FIG. 4. FIG. 4 shows the incorporation of a four layer permeable membrane into a scent release package. The package comprises two heat sealable panels 01 and 02. Panel 01 comprises a permeable membrane, a release layer and an impermeable portion. The permeable membrane is formed by layers 10, 11, 12a and 12b. Layer 13 is the release layer. The impermeable portion is comprised of layers 14, 15, 16 and 17.

The permeable membrane comprises a first sealable permeable layer 10, a second permeable layer 12b adhered to the first layer 10, a third permeable layer 11 adhered to the second layer 12b, a fourth permeable layer 12a adhered to the third permeable layer 11 and a release layer 13 adhered to the fourth layer 12a. Layer 13 is coextruded with the permeable membrane layers.

Layer 10 is permeable and cooperates with layers 11, 12a and 12b to provide the desired permeability of the membrane. Layer 10 comprises polymers and other components that provide permeability properties, good heat seal properties and good machinability to the outside layer of the membrane. Layer 10 is in contact with the aromatic product 30 and the material selected for layer 10 should have minimum interaction with the product 30. Examples of materials that are suitable for layer 10, include: polyethylene, EVA or other heat sealable resins. Machine Aids, such as antiblock and slip, may also be added to this layer.

Layer 11 forms the bulk of the membrane and has the greatest impact on the permeability of the membrane. Layer 11 is formed of resins having a high permeation rate for the aromatic product. Examples of materials which are suitable for layer 11, include: LDPE, VLDPE, EVA, ethylene-methyl acrylate copolymer and other available polymers, particularly more semi-crystaline polymers. Polymers of VLDPE having a density range between 0.870 g/cc and 0.900 g/cc are especially preferred. Layer 11 may also include blends of these polymers.

Layers 12a and 12b cooperate with layer 11 to provide the desired permeability. Layers 12a and 12b are connected internally in the extrusion equipment and are comprised of the same material. Layers 12a and 12b are formed from resins that provide a strong bond to layer 11 and a relatively weak bond to the release layer 13 to produce a peel laminate. Selection of the polymer for layers 12a and 12b depends upon the polymer selection for layer 13.

In a preferred embodiment of the invention, layer 13 is a nylon or EVOH and layers 12a and 12b are comprised of a modified polyolefin. In another preferred embodiment, layer 13 is a nylon or EVOH and layers 12a and 12b are a blend of LDPE and an adhesion promoting polyolefin, such as the modified polyolefin sold by Equistar under the trade name PLEXAR or ADMER sold by Mitsui.

Layer 13 is the release layer. Layer 13 cooperates with layer 12a to form the peel function. Layer 13 also provides barrier properties from the product. The release layer 13 is EVOH or nylon or copolymers of these resins.

The fourth permeable layer 12a is initially uniformly bonded to a release layer 13. The release layer 13 is comprised of a material that does not form strong heat bonds with the fourth permeable layer 12a at the same temperature at which bonds are formed between permeable layers 10 and 12b, permeable layers 12b and 11 and permeable layers 11 and 12a. For example, nylon or EVOH can be utilized as the release layer in conjunction with a modified polyethylene or EVA fourth permeable layer. It is further desired to coextrude the permeable membrane layers and the release layer material together at a fairly low temperature to provide a very uniform but weak bond between the release layer and the permeable membrane.

Layers 10, 11, 12a, 12b and 13 are cast coextruded and comprise a multilayer structure that is laminated to the impermeable portion of panel 01. The impermeable portion of panel 01 comprises layers 14, 15, 16 and 17. In one embodiment of the invention, layer 14 is a laminating extrusion resin, layer 15 is a foil, layer 16 is a polyethylene laminating resin and layer 17 is a polyester. In another preferred embodiment of the invention, the release layer 13 is bonded to layer 15 with a curing adhesive, 14.

Panel 02 is comprised of layers 20, 21, 22, 23 and 24. Layers 20, 21 and 22 form a nylon coextruded film. In a preferred embodiment, the nylon coextruded film comprises adhesive layers between the nylon layers. Layer 23 is an adhesive and layer 24 is a polyester, or acrylonitrile (BAREX) polymer, or a recycled polyester sheet. The nylon coextruded film is laminated to layer 24 by the adhesive layer 23.

The aromatic product 30 is held between layer 10 of panel 01 and layer 20 of panel 02. Layer 10 is heat sealed to layer 20. The bond formed between layer 10 and layer 20 is stronger than the bond formed between layer 12a and release layer 13.

Figure 5:
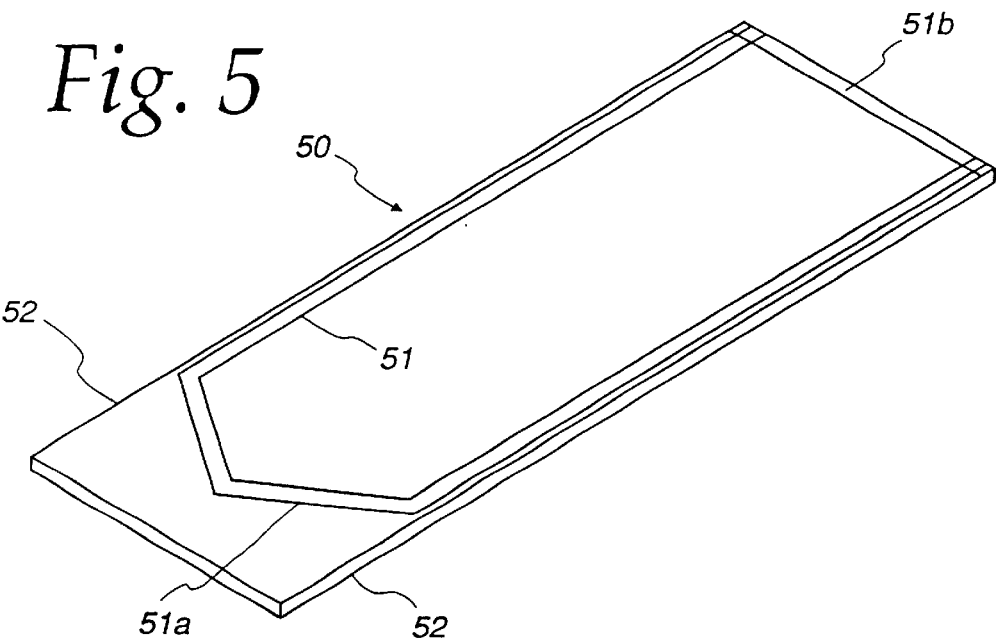
FIG. 5 is an exterior perspective view of a package, in accordance with this invention.
Figure 6:
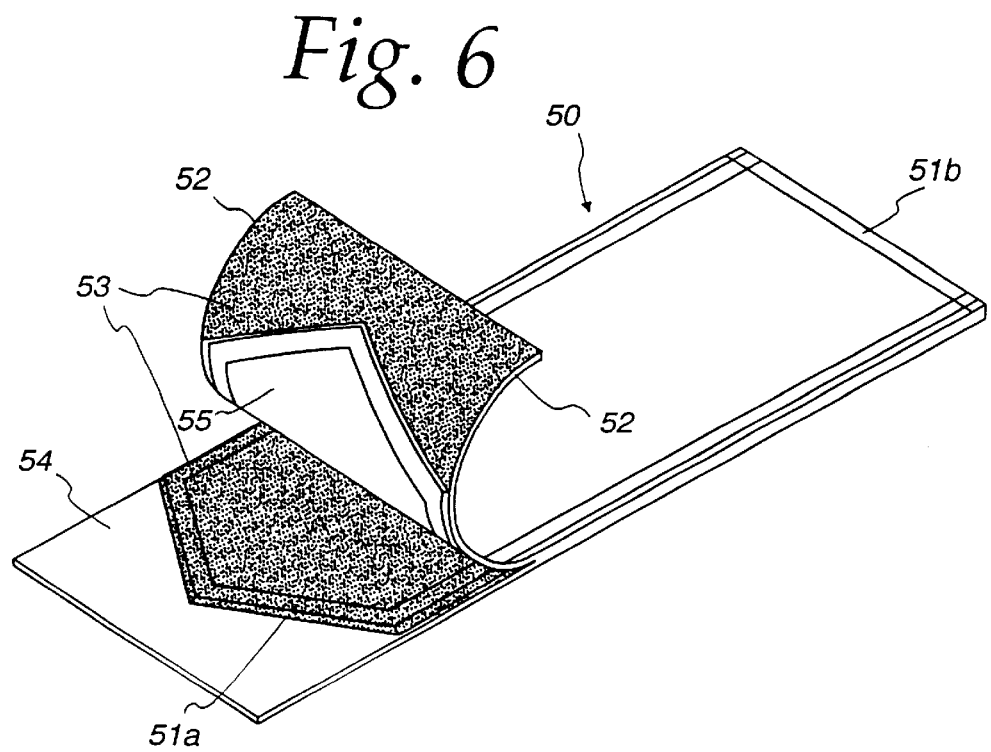
FIG. 6 is an exterior perspective illustrating opening function.

Referring to the drawings, a preferred embodiment of the present invention is a package for selectively providing controlled release of vapors from an aromatic product, as shown generally in an exterior view at 50 in FIG. 5. The package is shown in FIG. 5 in an unopened condition, in which the aromatic product is sealed within the package. The heat seal strip 51 surrounds the position of the aromatic product within the package. The package is opened by a user pulling apart the package at corners shown generally at 52 where the package has not been heat sealed and where there exists an interface between two panels of the layers of the package, which may be easily parted. FIG. 6 shows a partially opened package. In FIG. 6, 53 refers to the heat seal surfaces of the packages; 54 refers to the heat sealable panel 02; and 55 refers to the heat sealable panel 01.

The heat seal illustrated at 51 in FIG. 5 is formed to surround the aromatic product. However, it is not necessary that the entire bond be formed at the same time. For example, the V-shaped front and long sides of the bond can be formed initially. The aromatic product is then placed in the pocket formed between the heat sealable panels 01 and 02. An end seal 51b is then formed to complete the seal. The outer edge of the seal in general area a 51a has an impression formed in the membrane and sealant by a protrusion in the seal die. This impression or thinned area aids in separation of the membrane and release layer as the panels are separated at the chevron. The membrane, being tightly sealed to panel 02 remains with panel 02, thus covering the product. It is apparent that an aromatic product can be deposited directly in the initially formed pocket and sealed and thus, eliminate the need for a carrier pad.

The multilayer structures, which include a permeable membrane and a release layer, may be coextruded through any of several coextrusion methods that are common in the art, including cast coextrusion.

The following examples are provided as illustrative of the invention, but should not be construed as being exhaustive or as limiting the invention to the specific details thereof.

EXAMPLE 1

The multilayer structure was produced on a cast line. The first sealable permeable layer of the membrane was formed from hot melting and cast extruding 40 pounds per ream of a low density polyethylene, Quantum NA-206. The second permeable layer was formed of hot melting and cast extruding 20 pounds per ream of a blend of 95% Quantum NA-204 LDPE and 5% Quantum Plexar TR021, a maleic anhydride modified tie resin. The permeable layers were cast extruded with the release layers of 16 pounds per ream of Nylon 6, Allied 8207 at approximately 440° F. for the permeable membrane layers and 490° F. for the nylon. The bond between the LDPE in the second permeable layer and the nylon release layer was between 25 and 100 grams per inch.

The cast multilayer film was adhesive laminated to the foil layer of a non-permeable structure. The non-permeable structure was produced by extrusion laminating 48 g PET to 35 g aluminum foil using 15 pounds per ream of polyethylene. The completed structure thus provided a PET heat resistant outer layer, an aluminum barrier layer, a release layer and a permeable membrane.

Pouches were formed from two 2 inch by 5 inch panels of the laminated structure by heat sealing together the sealable membrane layers of the panels on three sides using a hot ribbon impulse sealer. Each pouch was filled with approximately 5 cc of a test fragrance product and the open fourth side of the pouch sealed. Over the course of eighteen months, the pouches were inspected for integrity and the non-permeable layer of various pouches was peeled away at the release layer to test function and inspect condition of the membrane layer. Package performed as designed.

EXAMPLE 2

The multilayer structure is produced on a cast line. The first sealable permeable layer of the membrane is formed from hot melting and cast extruding 15 pounds per ream of a low density polyethylene, Quantum NA-206. The second permeable layer is formed from hot melting and cast extruding 35 pounds per ream of very low density polyethylene, such as a FLEXOMER, which is a trade name of Union Carbide. The third permeable layer is formed from hot meeting and cast extruding 8 pounds per ream of a low density polyethylene, tie layer blend. 95% NA-206 and 5% PLEXAR TR021.

The permeable film is cast coextruded with the release layer of 16 pounds per ream of a nylon, Allied 8207, at approximately 440° F. for the low density polyethylene in the first permeable layer and 490° F. for the nylon. The bond between the low density polyethylene in the third permeable layer and the nylon in the release layer is between 25 and 100 g per 25.4 mm.

A seal is formed between the third permeable layer and the release layer by pressing the layers between a hot die and heated rubber backing on the bottom using A die temperature of approximately 485° F. applied for a sufficient period of time for the heat bonds to form (approximately 1 second.) The first permeable layer of the membrane was heat sealed to a thermoformed tray containing an aromatic product.

Upon opening the package, by pulling the release layer apart from the third permeable layer, the third permeable layer of low density polyethylene split apart uniformly along the line of weakness in a V-shape, leaving the membrane intact and sealed to the thermoformed tray. The fragrance could easily be detected, and a relatively uniform fragrance level was observed for a period of approximately 50 days after opening.

The weight loss of the fragrance was compared to the weight loss of the fragrance using a standard film membrane. The standard membrane is comprised of three permeable layers of a low density polyethylene. The weight loss of the new film shows a quicker initial release of fragrance and more weight loss over time than the standard film.

EXAMPLE 3

The multilayer structure is produced on a cast line. The first sealable permeable layer of the membrane is formed from hot melting and cast extruding 18 pounds per ream of a blend of 65% by weight of a very low density polyethylene, such as FLEXOMER, which is a tradename of Union Carbide, and 35% by weight of a low density polyethylene, Quantum NA-206. The second permeable layer is formed from hot melting and cast extruding 8 pounds per ream of a low density polyethylene, Quantum NA-206. The third permeable layer is formed from hot melting and cast extruding 30 pounds per ream of a blend of 73% by weight of a very low density polyethylene, such as Flexomer which is a trademark of Union Carbide and 27% by weight of a low density polyethylene, Quantum NA-206. The fourth permeable layer is formed from hot melting and cast extruding 8 pounds per ream of a low density polyethylene, Quantum NA-206.

The permeable film is cast coextruded with the release layer of 16 pounds per ream of nylon, Allied 8207 at approximately 440° F. for the low density polyethylene in the fourth permeable layer and 490° F. for the nylon. The bond between the low density polyethylene in the fourth permeable layer and the nylon in the release layer is between 25 g and 100 g.

The coextruded structure contains approximately the following dimensions: the release layer 1.0 mil, the fourth layer was 0.5 mil, the third layer was 2.0 mil, the second layer was 0.5 mil and the first sealable layer was 1.0 mil.

A seal is formed between the fourth permeable layer and the release layer by pressing the layers between a hot die and heated rubber backing on the bottom using a die temperature of approximately 485° F. applied for a sufficient period of time for the heat bonds to form (approximately 1 second). The first permeable layer of the membrane is heat sealed to a thermoformed tray containing an aromatic product.

Upon opening the package, by pulling the release layer apart from the third permeable layer, the third permeable layer of low density polyethylene split apart uniformly along the line of weakness in a V-shape, leaving the membrane intact and sealed to the thermoformed tray. The fragrance could easily be detected, and a substantially uniform fragrance level was observed for a period of approximately 50 days after opening.

The weight loss of the fragrance was compared to the weight loss of the fragrance using a standard film membrane. The standard membrane is comprised of three permeable layers of a low density polyethylene. The weight loss of the new film shows a quicker initial release of fragrance and, more weight loss over time than the standard film.

It is understood that the invention is not confined to the particular embodiments herein described as illustrative of the invention, but embraces all such modifications thereof as come with the scope of the following claims.

What is claimed is:

1. A multilayer structure for atmospheric diffusion of aromatic products wherein the structure comprises:

(a) a permeable membrane wherein said permeable membrane comprises at least two polymeric layers wherein the polymer of each layer is independently selected from the group consisting of polyethylene, very low density polyethylene, low density polyethylene, ethylene methylacrylate copolymer, ultra low density polyethylene and plastomer;

(b) a release layer wherein said release layer comprises a nylon polymer wherein the release layer is adhered to most inner polymeric layer of the permeable membrane and wherein the adhesion between the release layer and the adjacent layer of the polymeric permeable membrane is a relatively weak bond compared to the bond between the layers of the polymeric permeable membrane; and (c) an impermeable membrane wherein said impermeable membrane comprises one or more layers wherein the individual layers of the impermeable membrane are independently selected from the group consisting of metal, foil and poly (ethylene terephalate) and wherein said impermeable portion is laminated to said release layer.

* * * * *